United States Patent [19]
Hiestand

[11] 3,940,435
[45] Feb. 24, 1976

[54] PERFLUOROALKYL COMPOUNDS
[75] Inventor: Armin Hiestand, Binningen, Switzerland
[73] Assignee: Ciba-Geigy Corporation, Ardsley, N.Y.
[22] Filed: Sept. 10, 1973
[21] Appl. No.: 395,811

[30] Foreign Application Priority Data
Sept. 15, 1972  Switzerland........................ 13548/72
Feb. 2, 1973    Switzerland.......................... 1560/73

[52] U.S. Cl...... 260/481 R; 260/465 G; 260/539 R; 260/561 S; 252/8.7
[51] Int. Cl.$^2$............... C07C 147/02; C07C 147/14
[58] Field of Search........ 260/481 R, 539 R, 539 A, 260/561 S; 252/400

[56] References Cited
UNITED STATES PATENTS

| | | | |
|---|---|---|---|
| 2,892,852 | 6/1959 | Koenig et al.......................... | 260/400 |
| 2,892,853 | 6/1959 | Koenig et al.......................... | 260/400 |
| 3,172,910 | 3/1965 | Brace............................... | 260/481 R |
| 3,758,531 | 7/1973 | Koshar............................. | 260/481 R |

OTHER PUBLICATIONS
Larsson, C.A. 42 7248e.
Orda et al. C.A. 63 1684h (1965).
Orda et al. C.A. 63 17861c (1965).
Orsymonde C.A. 66 P 65110t (1967).

Primary Examiner—John F. Terapane
Attorney, Agent, or Firm—Joseph G. Kolodny; Prabodh I. Almaula; Edward McC. Roberts

[57]    ABSTRACT

New perfluoroalkyl compounds of the formula
$$R_f-CH_2CH_2-SO_xC_mH_{2m}A,$$
wherein $R_f$ is a perfluoroalkyl radical with 5 to 18 carbon atoms, A is carboxyl, carboxyl ester, carboxylic amide or cyano, $x$ is 1 or 2 and $m$ is a whole number from 1 to 3, with the proviso that when A is carboxyl, then m is only 1 if $x$ is 1, are provided.

These new compounds are useful for producing oleophobic finishes on porous and non-porous substrates, e.g. textile materials. They are also useful as intermediates for the manufacture of further fluorine containing finishing agents.

11 Claims, No Drawings

PERFLUOROALKYL COMPOUNDS

The present invention provides perfluoroalkyl compounds of the formula $$R_f-CH_2CH_2-SO_x-C_mH_{2m}A \quad (1)$$

wherein $R_f$ is a perfluoroalkyl radical with 5 to 18 carbon atoms, A is carboxyl, carboxyl ester, carboxylic amide or cyano, $x$ is 1 or 2 and $m$ is a whole number from 1 to 3, with the proviso that when A is carboxyl, then $m$ is only 1 if $x$ is 1. When A is carboxyl and $x$ is 2, then $m$ can only be 2 or 3.

Preferably the perfluoroalkyl compounds according to the invention correspond to the formula $$C_nF_{2n+1}-CH_2CH_2-SO_x-C_mH_{2m}A_1 \quad (2)$$

wherein $A_1$ is —COOH, —COOR,

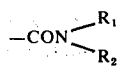

or —CN, R is alkyl with 1 to 20, preferably 1 to 18, carbon atoms, and $R_1$ and $R_2$ each independently represents hydrogen or alkyl with 1 to 20, preferably 1 to 18, carbon atoms, $n$ is a whole number from 6 to 14, preferably 6 to 10, $x$ is 1 or 2 and $m$ is a whole number from 1 to 3, with the proviso that when $A_1$ is carboxyl, then $m$ is only 1 if $x$ is 1.

The perfluoroalkyl radical can be straight-chain or branched and comprises, for example, the following radicals:

$C_6F_{13}$—, $C_8F_{17}$—, $C_{10}F_{21}$—, $C_{12}F_{25}$—, $C_{14}F_{29}$—, $C_{16}F_{33}$—, $C_{18}F_{37}$— or also $(CF_3)_2CF(CF_2)_{n'}$—, wherein $n'$ is a whole number from 2 to 15.

The radical $A_1$ represents the free carboxyl group —COOH, optionally —COOM, wherein M can represent e.g. alkali metal or ammonium, the cyano group —CN and the carboxylic amide group —CONH$_2$. This last mentioned group can be substituted with alkyl groups which contain 1 to 20, preferably 1 to 18, carbon atoms. These alkyl-substituted carboxylic amide groups correspond to the formulae

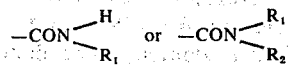

wherein $R_1$ and $R_2$ have the indicated meaning and can also represent the same alkyl radical. Particularly valuable compounds are also those in which $R_1$ is hydrogen and $R_2$ is alkyl with 16 to 18 carbon atoms.

In the carboxyl ester groups —COOR the alkyl radicals can also contain 1 to 20, preferably 1 to 18, carbon atoms. Suitable alkyl radicals in the carboxylic amide and carboxyl ester groups are, for example, methyl, ethyl, propyl, butyl, amyl, heptyl, octyl, nonyl, decyl, dodecyl, tetradecyl, hexadecyl, and octadecyl.

Suitable compounds according to formula (2) correspond to the following formulae $$C_nF_{2n+1}-CH_2CH_2-SO_x-C_mH_{2m}COOH \quad (3)$$

$$C_nF_{2n+1}-CH_2CH_2-SO-C_mH_{2m}COOH \quad (4)$$

$$C_nF_{2n+1}-CH_2CH_2-SO_2-C_mH_{2m}COOH \quad (5)$$

$$C_nF_{2n+1}-CH_2CH_2-SO_x-C_mH_{2m}COOR \quad (6)$$

$$C_nF_{2n+1}-CH_2CH_2-SO-C_mH_{2m}COOR \quad (7)$$

$$C_nF_{2n+1}-CH_2CH_2-SO_2-C_mH_{2m}COOR \quad (8)$$

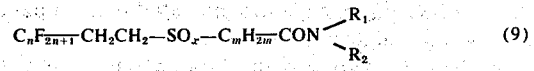
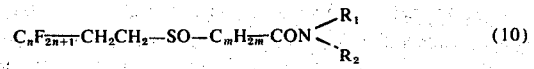
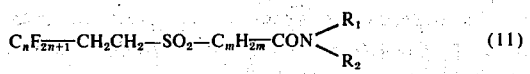

$$C_nF_{2n+1}-CH_2CH_2-SO_x-C_mH_{2m}CN \quad (12)$$

$$C_nF_{2n+1}-CH_2CH_2-SO-C_mH_{2m}CN \quad (13)$$

$$C_nF_{2n+1}-CH_2CH_2-SO_2-C_mH_{2m}CN \quad (14)$$

wherein R represents alkyl with 1 to 20, preferably 1 to 18, carbon atoms, and $R_1$ and $R_2$ each independently represents hydrogen or alkyl with 1 to 20, preferably 1 to 18, carbon atoms, $n$ is a number from 6 to 14, preferably from 6 to 10, $x$ is 1 or 2, $m$ is a whole number from 1 to 3, and in the compounds (3) to (5) $m$ is only 1 if $x$ is 1. Preferably branched radicals $C_mH_{2m}$ are suitable when $m$ is 3.

Particularly valuable compounds are those of the formulae $$C_nF_{2n+1}-CH_2CH_2-SO_x(CH_2)_{m'}-A_2 \quad (15a)$$

$$C_nF_{2n+1}-CH_2CH_2-S(O)_x(CH_2)_{m'}-A_2 \quad (15b)$$

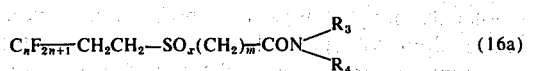
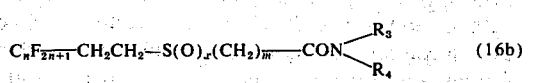

wherein $A_2$ is —COOH, —CONH$_2$ or —CN, $m$, $n$, and $x$ have the indicated meanings, $m'$ is 1 or 2, with the proviso that when $A_2$ is carboxyl, then $m'$ is only 1 if $x$ is 1, and $R_3$ and $R_4$ each independently represents hydrogen or alkyl with 1 to 10 carbon atoms.

The following compounds may also be cited:

$$C_nF_{2n+1}-CH_2CH_2-SO-CH_2-COOH$$

$$-CH_2CH_2-$$

$$-CH-CH_2-$$
$$\quad \vert$$
$$\quad CH_3$$

$$-CH_2CH-$$
$$\quad \vert$$
$$\quad CH_3$$

$$-CH-CH_2-$$
$$\quad \vert$$
$$\quad CH_3$$

$$-CH_2-CH-$$
$$\quad\quad\vert$$
$$\quad\quad CH_3$$

Analogous groups of formulae also apply to the compounds which contain the radicals —COOR$_1$, —CONH$_2$, and —CN.

The compounds according to the invention are manufactured by oxidation of the thioether compounds known from U.S. Pat. No. 3,172,910, of the formula $$R_f-CH_2CH_2-S(CH_2)_{m'}A \quad (17)$$

wherein $R_f$ and A have the indicated meaning and $m''$ is a whole number from 1 to 3.

Suitable for carrying out the reaction are the known oxidants, preferably hydrogen peroxide. The thioether compounds can be dissolved in organic solvents, for example halogenated hydrocarbons such as trichlorotrifluoroethane, preferably in concentrated acetic acid, and the oxidant is added slowly with vigorous stirring, so that during the manufacture of a sulphoxide compound the temperature remains between about 40° and 50°C; but during the manufacture of a sulphone compound the temperature remains in a first step at about 50° to 60°C, then in a second step at about 100° to 110°C. The addition of the oxidant can take, for example, 15 to 60 minutes. In order to bring the reaction to completion it is possible to leave the reaction mixture subsequently for a period of time at the indicated temperatures.

The resulting compounds according to the invention are insoluble in water, and also in organic solvents they are soluble only in small amounts, but sufficiently so to effect applications from solvents.

Examples of suitable solvents are halogenated aliphatic hydrocarbons, e.g. trichloroethane, perchloroethylene, chloroform, methylene chloride, carbon tetrachloride, dibromoethylene, and the chlorinated and fluorinated ethanes, such as 1,1-dichloroethane, 1,2-dichloroethane, 1,1,1-trichloroethane, 1,1,2,2-tetrachloroethane, trichlorotrifluoroethane, halogenated benzenes and optionally benzenes substituted with low molecular alkyl groups, e.g. mono- and dichlorobenzene, chlorotoluenes, ethers such as diethyl ether, diisopropyl ether, dioxan and tetrahydrofuran, diethoxyethane, ketones, such as acetone, methyl ethyl ketone, cyclohexanone; also esters, e.g. ethyl acetate, dimethyl formamide, dimethyl acetamide, fluorine-containing alcohols, e.g. hexafluoroisopropanol, tetrafluoropropanol, octafluoropentanol, etc. It is also possible to use mixtures of the cited solvents.

Owing to their perfluoroalkyl concentration the compounds according to the invention are suitable for producing oleophobic finishes on porous and non-porous substrates. They can be used furthermore as intermediates for the manufacture of further fluorine compounds.

Simultaneously there are obtained hydrophobic effects which are intensified by using carboxyl esters or carboxylic amides with long-chain alkyl chains, for example those with 8 to 20 and 8 to 18 carbon atoms. By porous substrates are meant for example leather, paper, and wood, but preferably textile fibre materials; suitable non-porous materials are glass, metal, and plastic surfaces. The compounds according to the invention can also be used, for example, as additives for oils and lubricants for the prevention of wear and corrosion, or as additives for polishes and waxes.

The compounds according to the invention can be used very particularly for finishing textile materials, for example those made from natural or regenerated cellulose, such as cotton, linen, staple fibre, or cellulose acetate; also those made from wool, synthetic polyamides, polyesters, polypropylene, and polyacrylonitrile, as well as the corresponding fibre blends.

The textile materials can be in any desired form of processing, for example as fibres, threads, tops, woven or knitted fabrics.

The compounds according to the invention are applied from solvent liquors by the immersion process, also by padding, spraying, slop-padding, immersion in a melt, spraying with heat fixing or also by transfer from an auxilary material (paper, foil) accompanied by the application of heat.

The temperature range for the application from solvents is as a rule between 20° and 110°C, preferably between 40° and 80°C. The treatment times can be between 1 and 30, preferably between 5 and 15, minutes. For the other methods of application it is necessary to apply in general temperatures which lie above the melting points of the compounds according to the invention.

The substrates which are finished with the compounds according to the invention exhibit good oil repellency and are also hydrophobic. The effects are obtained by applying the compounds according to the invention in amounts from about 0.05 to 10, preferably from 0.1 to 5, percent by weight, based on the weight of the substrates. A particular advantage of the new sulphoxide and sulphone compounds resides in the substantially improved stability to hydrolysis compared with the thioether compounds used as starting materials.

The following Examples illustrate the invention, the parts and percentages being by weight unless otherwise stated. The perfluoralkyl radical in the following Examples has the following composition:

| | |
|---|---|
| $C_8F_{17}$ | 45% |
| $C_6F_{13}$ | 25% |
| $C_{10}F_{21}$ | 25% | higher homologues ~ 5%.

Example 1

82.4 g (153 mmols) of

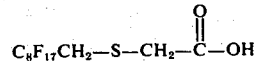

are dissolved in 150 ml of glacial acetic acid. The solution is heated to 35°C with stirring. Within ¾ hour 19.4 g of $H_2O_2$ (35%) (200 mmols) are added, in the process of which the temperature rises from 35° to 50°C. Upon completion of the dropwise addition a precipitate falls out. The batch is allowed to cool and the glacial acetic is then removed at 70°C under reduced pressure. The substance is then dried over $CaCl_2$ and concentrated $H_2SO_4$.

Yield: 82.9 g (98% of theory) of the compound of the formula

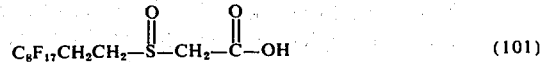 (101)

m.p.: 95° to 115°C.

calculated: C 26.01; H 1.27; F 58.27; S 5.78; found: C 26.6; H 1.4; F 58.8; S 5.8;

Example 2

44.2 g (80 mmols) of

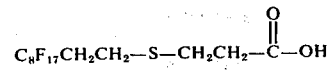

are dissolved in 100 ml of glacial acetic acid and the solution is then heated with stirring to 35° to 40°C. 11.65 g (120 mmols) of $H_2O_2$ (35%) are then added within one-half hour. The rising reaction temperature caused by the exothermic reaction is kept in the range of 45° to 48°C by cooling. Then the batch is allowed to continue to react for 2 hours at 40° to 45°C and subsequently cooled, in the course of which the product falls out. The precipitate is isolated and dried over $CaCl_2$ and concentrated $H_2SO_4$.

Yield: 40.8 g (89.5% of theory) of the compound of the formula

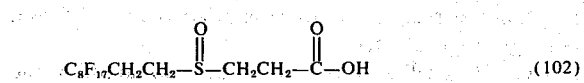 (102)

m.p.: 127° to 134°C calculated: C 27.48; H 1.60; F 56.84; S 5.64; found: C 27.2; H 1.6; F 56.3; S 5.8.

Example 3

71.7 g (130 mmols) of

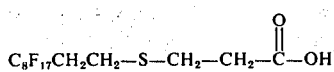

are dissolved in 200 ml of glacial acetic acid and the solution is heated with stirring to 35° to 40°C. 37.9 g (390 mmols) of $H_2O_2$ (35%) are then added within three-fourths hour. The reaction proceeds in two stages. During the addition of the first third of $H_2O_2$ an exothermic reaction occurs up to 70°C. This then subsides. The reaction mixture is subsequently heated to 100°C using an oil bath and the remainder of the $H_2O_2$ is added, in the course of which an exothermic reaction occurs once more (100° to 110°C). Upon completion of the addition the product begins to precipitate. The batch is allowed to stand for about 1 day, then the product is isolated and dried over $CaCl_2$ and concentrated $H_2SO_4$.

Yield: 73.8 g (97.1% of theory) of the compound of the formula

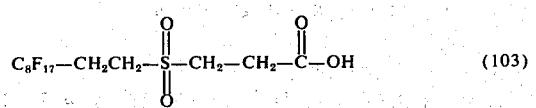 (103)

m.p.: 165° to 170°C (brown colouration).

calculated: C 26.73; H 1.55; F 55.28; S 5.8; found: C 26.5; H 1.5; F 55.2; S 5.8;

Example 4

80.5 g (150 mmols) of

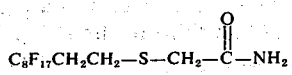

are dissolved with stirring in 250 ml of glacial acetic acid, and the solution is then heated to 30°C. 21.85 g (225 mmols) of $H_2O_2$ (35%) are added within one-half hour. The exothermic reaction is halted at a maximum temperature of 45°C. Subsequently the reaction is allowed to continue for 2 hours at 40° to 45°C. The reaction mixture is then allowed to cool and the reaction product crystallises out. After 1 day the crystals are isolated and dried over $CaCl_2$ and concentrated $H_2SO_4$.

Yield: 27.2 g (32.7% of theory) of the compound of the formula

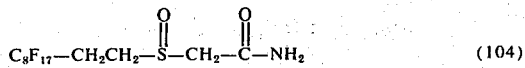 (104)

m.p.: 150° to 164°C.

calculated: C 26.05; H 1.46; N 2.53; F 58.38; S 5.80; found: C 25.9; H 1.5; N 2.8; F 59.3; S 5.1;

The 2nd fraction is obtained by evaporating the glacial acetic acid filtrate (main fraction). It is also dried in an exsiccator over $CaCl_2$ and concentrated $H_2SO_4$.

Yield: 49.2 (59.2% of theory); pale yellow powder; m.p. 120° to 160°C.

Example 5

80.5 g (150 mmols) of

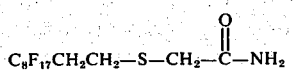

are dissolved with stirring in 250 ml of glacial acetic acid and the solution is then heated to 45°C. 43.7 g (450 mmols) of $H_2O_2$ (35%) are added within one-half hour. The reaction proceeds in two stages. An exothermic reaction sets in up to 75°C during the addition of the first third of the $H_2O_2$. The reaction mixture is then heated to 100°C internal temperature and the remainder of the $H_2O_2$ is added, when once again exothermic reaction occurs (up to 105°C). The reaction is subsequently kept for 1½ hours at 100° to 105°C. After it has cooled the reaction mixture is left standing for 1 day during which time the reaction product precipitates. This is then isolated and dried over $CaCl_2$ and concentrated $H_2SO_4$.

Yield: 48.4 g (56.8% of theory) of the compound of the formula

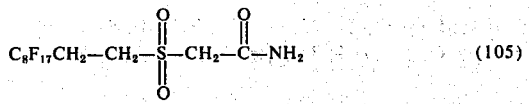 (105)

m.p.: 110° to 140°C.

calculated: C 25.32; H 1.42; N 2.46; S 5.63; F 56.74; found: C 24.3; H 1.4; N 2.4; S 5.5; F 57.8;

Example 6

82.7 g (150 mmols) of

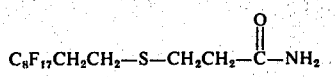

are dissolved in 150 ml of glacial acetic acid at an internal temperature of 35°C. 21.85 g (225 mmols) of $H_2O_2$ (35%) are added within 15 minutes, in the course of which the rise in temperature induced by the exothermic reaction is kept in the range of 45°C by cooling. The reaction mixture is subsequently allowed to continue to react for 2 hours at 43° to 45°C. Then the glacial acetic acid is isolated under reduced pressure at 45°C (water jet vacuum). The residual product is dried over CaCl₂ and H₂SO₄ (conc.).

Yield: 84.6 g (99.5% of theory) of the compound of the formula

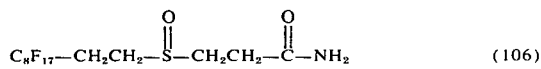 (106)

m.p.: 125° to 153°C.

calculated: C 27.53; H 1.78; N 2.47; S 5.65; F 56.93; found: C 27.4; H 1.9; N 2.5; S 5.6; F 56.6;

Example 7

82.6 g (150 mmols) of

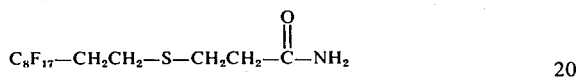

are dissolved with stirring in 250 ml of glacial acetic acid, and the solution is then heated to 35° to 45°C. 43.7 g (450 mmols) of H₂O₂ (35%) are then added within one-half hour. The reaction proceeds in two stages. Exothermic reaction occurs up to 75°C during the addition of the first third of the H₂O₂. The reaction mixture is then heated to 100°C and the remainder of the H₂O₂ is added, when once more exothermic reaction occurs (100° to 108°C). The reaction mixture is stirred for 2 hours at 100° to 105°C. After it has cooled, the reaction mixture is allowed to stand for about 1 day. The precipitated product is then isolated and dried over CaCl₂ and concentrated H₂SO₄.

Yield: 76 g (87.9% of theory) of the compound of the formula

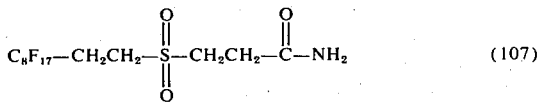 (107)

m.p.: 155° to 170°C.

calculated: C 26.77; H 1.73; N 2.40; S 5.50; F 55.37; found: C 26.57; H 1.67; N 2.22; S 5.23; F 54.9;

Example 8

25.9 g (50 mmols) of C₈F₁₇—CH₂CH₂—S—CH₂—C≡N are dissolved in 50 ml of glacial acetic acid at 35° to 40°C. Then 7.2 g (75 mmols) of H₂O₂ (35%) are added over 10 minutes. The temperature is kept in the range up to 45°C. Stirring is subsequently continued for 2 hours at 40° to 45°C. The glacial acetic acid is isolated at 40° to 45°C bath temperature under reduced pressure. The resulting product is dried over CaCl₂ and H₂SO₄ (conc.).

Yield: 25.3 g (95% of theory) of the compound of the formula

 (108)

m.p.: 120° to 135°C (brown colouration).

calculated: C 26.93; H 1.13; N 2.62; S 5.99; F 60.34; found: C 26.86; H 1.11; N 3.14; S 6.26; F 59.20;

Example 9

25.9 g (50 mmols) of C₈F₁₇—CH₂CH₂—S—CH₂—C≡N are dissolved at 40°C in 50 ml of glacial acetic acid. Then 14.58 g (150 mmols) of H₂O₂ (35%) are added in 15 minutes. The addition takes place in 2 equal portions: the first portion at 40°C, when exothermic reaction occurs up to 60°C, with subsequent heating to 100°C, and then the second portion is added, when exothermic reaction occurs up to 104°C. The colour of the reaction mixture changes from reddish brown to pale yellow. Subsequently the reaction is kept for 2 hours at 100°C to 105°C. Upon completion of the reaction the reaction mixture is dried over CaCl₂ and concentrated H₂SO₄.

Yield: 27 g (98% of theory) of the compound of the formula

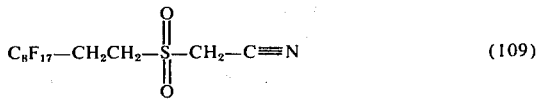 (109)

m.p.: 145° to 170°C.

calculated: C 26.15; H 1.10; N 2.54; S 5.82; F 58.59; found: C 25.88; H 1.30; N 2.83; S 5.56; F 58.5;

Example 10

81.6 g (153 mmols) of C₈F₁₇—CH₂CH₂—S—CH₂—C≡N are dissolved in 100 ml of trifluorotrichlorethane and the solution is heated with stirring to 45°–48°C. Then 31.4 g (324 mmols) of a solution of 31.4 g (324 mmols) of H₂O₂ in 30 ml of glacial acetic acid are added. The reaction proceeds exothermically and the solvent is refluxed. Upon completion of the addition the reaction is maintained for 1 hour at 48°C. The reaction mixture is processed by treating it with 300 ml of water, in the course of which the product precipitates. This is isolated and dried over CaCl₂ and concentrated H₂SO₄.

Yield: 76.7 g (88.8% of theory) of the compound of the formula

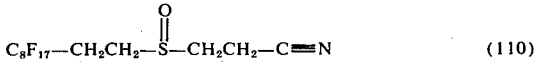 (110)

m.p.: 115° to 130°C.

calculated: C 28.43; H 1.47; N 2.55; S 5.84; F 58.80; found: C 28.27; H 1.34; N 2.65; S 5.93; F 58.6;

Example 11

78.9 g (148 mmols) of C₈F₁₇—CH₂CH₂—S—CH₂—C≡N are disolved in 250 ml of glacial acetic acid and the solution is heated to 30°C with stirring. Then 43.7 g (450 mmols) of H₂O₂ (35%) are added thereto within 30 minutes. The reaction proceeds in two stages. Exothermic reaction occurs up to 62°C during the dropwise addition of the first third of the H₂O₂. Then the reaction mixture is heated to 100°C internal temperature and the remainder of the H₂O₂ is added, when exothermic reaction occurs up to 106°C. Stirring is subsequently continued for 2 hours at 100° to 103°C. After the reaction mixture has cooled it is allowed to stand for 1 day, when the product precipitates. The precipitate is isolated and dried over CaCl₂ and H₂SO₄ (conc.).

Yield: 71.1 g (85% of theory) of the compound of the formula

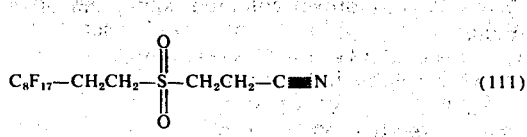 (111)

m.p.: 150° to 175°C.
calculated: C 27.62; H 1.43; N 2.48; S 5.67; F 57.14; found: C 27.42; H 1.63; N 2.53; S 5.47; F 56.88.

Example 12

28.3 g (50 mmols) of

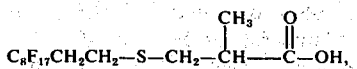

manufactured by addition of $C_8F_{17}CH_2CH_2SH$ to methacrylic acid by a process analogous to that according to U.S. Pat. No. 3,172,910, are dissolved in 80 ml of glacial acetic acid, and the solution is then heated to 35° to 40°C. 14.6 g (150 mmols) of $H_2O_2$ (35%) are added within three-fourths hour. The reaction proceeds in two stages. The temperature rises to the region of 50°C during the addition of the first third of the $H_2O_2$ and this exothermic reaction then subsides. The reaction mixture is subsequently heated to 80°–85°C using an oil bath and the remainder of the $H_2O_2$ is added, when exothermic reaction once more occurs and the temperature rises to 107°C. The contents of the flask are concentrated in vacuo and the residue is treated with ethyl acetate. Once more the contents are evaporated to dryness.

Yield: 27.6 g (92.2% of theory) of the compound of the formula

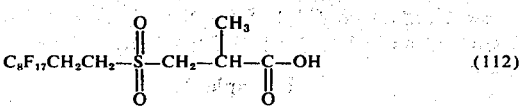 (112)

m.p.: 116° to 120°C with brown colouration
calculated: C 28.25; H 1.84; F 54.0; S 5.35; found: C 28.4; H 1.9; F 53.8; S 5.1.

Example 13

28.3 g (50 mmols) of

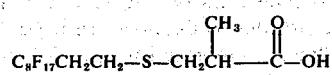

are dissolved in 80 ml of glacial acetic acid and the solution is then heated with stirring to 35°–40°C. The 7.3 g (75 mmols) of $H_2O_2$ (35%) are added within one-half hour. The rising reaction temperature caused by the exothermic reaction is kept in the range from 45°–48°C by cooling. The reaction is subsequently allowed to continue for 25 hours at 40°–45°C. The contents of the flask are concentrated in vacuo, then the residue is dissolved in ethyl acetate and this solution is evaporated to dryness in vacuo.

Yield: 27.1 g (94.8% of theory) of the compound of the formula

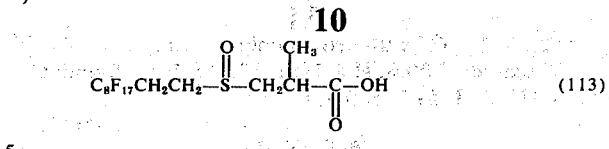 (113)

m.p.: 92° to 98°C.
calculated: C 28.79; H 1.89; F 55.5; S 5.50; found: C 29.1; H 1.9; F 55.1; S 5.2.

Example 14

100 g (173 mmols) of

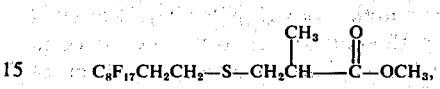

manufactured by addition of $C_8F_{17}CH_2CH_2SH$ to methacrylic methyl ester by a method analogous to that according to U.S. Pat. No. 3,172,910, are dissolved in 100 ml of glacial acetic acid and this solution is then heated to 35°–40°C with stirring. Then 23.6 g (244 mmols) of $H_2O_2$ (35%) are added within one-half hour. The rising reaction temperature caused by the exothermic is kept in the range from 45°–48°C by cooling. Subsequently the reaction is allowed to continue for 15 hours at 40°–45°C. The contents of the flask are concentrated in vacuo and the residue is taken up in ethyl acetate and this solution is evaporated to dryness in vacuo.

Yield: 98.2 g (95.3% of theory) of the compound of the formula

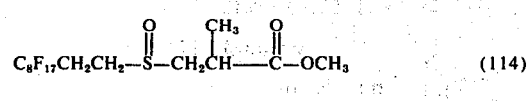 (114)

m.p.: 55° to 60°C.
calculated: C 30.1; H 2.2; F 54.3; S 5.37; found: C 30.4; H 2.18; F 53.4; S 5.2.

Example 15

100 g (173 mmols) of

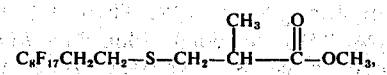

are dissolved in 200 ml of glacial acetic acid and this solution is then heated with stirring to 35°–40°C. The 47.2 g (485 mmols) of $H_2O_2$ (35%) are added within three-fourths hour. The reaction proceeds in two stages. An exothermic reaction occurs during the addition of the first third of the $H_2O_2$ and this then subsides. The reaction mixture is subsequently heated to 100°C using an oil bath and the remainder of the $H_2O_2$ is added, when once more an exothermic reaction occurs (100°–110°C). The contents of the flask are concentrated in vacuo and the residue is treated with ethyl acetate. The contents are then evaporated to dryness once more.

Yield: 98.5 g (93.0% of theory) of the compound of the formula

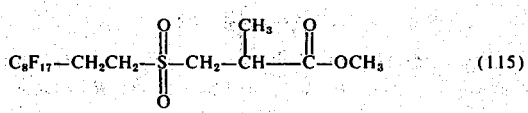 (115)

m.p.: 85°–90°C with brown colouration.

calculated: C 29.6; H 2.14; F 52.6; S 5.23; found: C 29.8; H 2.3; F 51.8; S 5.3;

Example 16

47.5 g (80 mmols) of

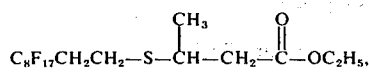

manufactured by addition of $C_8F_{17}CH_2CH_2SH$ to ethyl crotonate by a method analogous to that described in U.S. Pat. No. 3,172,910, are dissolved in 100 ml of glacial acetic acid. This solution is then heated with stirring to 35°–40°C. Then 11.65 g (120 mmols) of $H_2O_2$ (35%) are added within one-half hour. The rising reaction temperature caused by the exothermic reaction is kept in the range from 45°–48°C by cooling. Subsequently the reaction is allowed to continue for 18 hours at 40°–45°C.

Yield: 47 g (96% of theory) of the compound of the formula

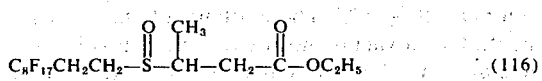

m.p.: 53° to 57°C.

calculated: C 31.60; H 2.48; F 53.00; S 5.25; found: C 31.7; H 2.6; F 52.8; S 5.0.

Example 17

47.5 g (80 mmols) of

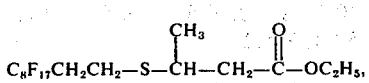

are dissolved in glacial acetic acid and this solution is then heated with stirring to 35°–40°C. Then 23.3 g (240 mmols) of $H_2O_2$ (35%) are added within three-fourths hour. The reaction proceeds in two stages. An exothermic reaction occurs at 70°C during the addition of the first third of the $H_2O_2$ and this then subsides. The reaction mixture is subsequently heated to 100°C using an oil bath and the remainder of the $H_2O_2$ is added, when once more an exothermic reaction occurs (100°–110°C).

Yield: 48.5 g (97% of theory) of the compound of the formula

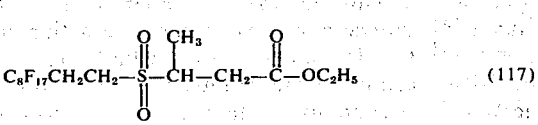

m.p. 65°–68°C with brown colouration.

calculated: C 30.85; H 2.43; F 51.6; S 5.1; found: C 31.1; H 2.5; F 51.3; S 4.9.

Example 18

Over a period of 17 hours and in an atmosphere of nitrogen, 27.2 g (50 mmols) of $C_8F_{17}$—$CH_2C$-$H_2$—SO—$CH_2COOH$ are brought to reaction in a melt at 150°C with 13.5 g (50 mmols) of 1-octadecanol, to give a slightly brown coloured compound of the formula

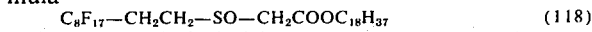

which is soluble in hot benzene.

Yield: 38.3 g (97.3% of theory).

m.p.: 65° to 130°C.

calculated: C 44.67; H 5.37; F 40.04; S 3.97; found: C 44.49; H 5.45; F 39.6; S 3.91.

Example 19

It is also possible to manufacture the product according to Example 18 in the following way:

3.9 g (5 mmols) of $C_8F_{17}CH_2CH_2$—S—$CH_2COOC_{18}H_{37}$ are dissolved in 60 ml of glacial acetic acid. Then this solution is heated with stirring to 60°C and 0.73 g (7.5 mmols) of $H_2O_2$ (35%) is added thereto. The reaction mixture is stirred for 1 hour and the glacial acetic acid is removed at 70°C under reduced pressure. The residue is boiled repeatedly in benzene and the solvent removed to give 4 g of the compound of the formula

Yield: 99.5% of theory.

Example 20

3.9 g (5 mmols) of $C_8F_{17}$—$CH_2CH_2$—S—$CH_2$—CO—$NH(CH_2)_{17}CH_3$ are dissolved in 25 ml of glacial acetic acid. This solution is then heated with stirring to 55°C and 0.73 g (7.5 mmols) of $H_2O_2$ (35%) is added thereto. The reaction mixture is stirred for 1 hour at 55°–60°C and the glacial acetic acid is then removed at 70°C under reduced pressure. The residue is repeatedly dissolved in benzene and the solvent evaporated to give 4 g of the colourless compound of the formula

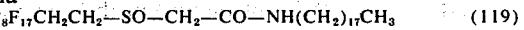

Yield: 99.5% of theory.

m.p.: 123° to 127°C.

calculated: C 44.72; H 5.50; N 1.74; S 3.98; F 40.08; found: C 44.2; H 5.47; N 1.78; S 3.90; F 39.6.

Example 21

3.9 g (5 mmols) of $C_8F_{17}CH_2CH_2$—S—$CH_2COO(CH_2)_{17}CH_3$ are dissolved in 60 ml of glacial acetic acid. This solution is then heated with stirring to 60°C and 0.73 g (7.5 mmols) of $H_2O_2$ is added thereto. The reaction mixture is stirred for one-half hour at 60° to 65°C and then once more 0.73 g (7.5 mmols) of $H_2O_2$ is added and the mixture is heated to 95°C. The batch is then stirred for 1 hour at 100°–105°C and the glacial acetic acid is then removed at 35°C under reduced pressure. The residue is dissolved repeatedly in benzene and the solvent evaporated to give 3.3 g of a compound of the formula

Yield: 80.4% of theory.

m.p.: 60° to 85°C.

calculated: C 43.80; H 5.27; S 3.90; F 39.26; found: C 42.9; H 5.2; S 4.0; F 38.8;

Example 22

3.9 g (5 mmols) of $C_8F_{17}CH_2CH_2$—S—$CH_2$—CO—$NH(CH_2)_{17}CH_3$ are dissolved in 60 ml of glacial acetic acid. This solution is then heated with stirring to 60°C and 0.73 g (7.5 mmols) of $H_2O_2$ (35%) is added thereto. The reaction mixture is stirred for one-half hour at 60°–65°C and then once more 0.73 g (7.5 mmols) of $H_2O_2$ is added and the batch is heated to 95°C. After stirring for 1 hour at 100°–105°C the glacial acetic acid is removed at 55°C under reduced pressure. The residue is dissolved repeatedly in benzene and the solvent evaporated to give 4.05 g (98.7% of theory) of the compound of the formula $$C_8F_{17}\text{—}CH_2CH_2\text{—}SO_2\text{—}CH_2\text{—}CO\text{—}NH(CH_2)_{17}CH_3 \quad (121)$$

m.p.: 130° to 135°C calculated: C 43.85; H 5.40; N 1.70; S 3.90; F 39.30; found: C 43.2; H 5.32; N 1.77; S 3.86; F 38.7.

Example 23

Over a period of 17 hours and in an atmosphere of nitrogen 29.2 g (50 mmols) of $C_8F_{17}CH_2CH_2\text{—}SO_2CH_2CH_2COOH$, obtained according to Example 3, are brought to reaction in a melt at 150°C with 13.5 g (50 mmols) of 1-octadecanol, to give a dark brown pulverulent compound of the formula $$C_8F_{17}\text{—}CH_2\text{—}CH_2\text{—}SO_2\text{—}CH_2\text{—}CH_2\text{—}COO(CH_2)_{17}CH_3 \quad (122)$$

Yield: 40.7 g (97.3% of theory).

m.p.: 106° to 115°C calculated: C 44.80; H 5.42; S 3.83; F 38.60; found: C 44.80; H 5.52; S 4.06; F 38.2

Example 24

Over a period of 5 hours an in an atmosphere of nitrogen 29.2 g (50 mmols) of $C_8F_{17}\text{—}CH_2CH_2\text{—}SO_2\text{—}CH_2\text{—}COOH$, obtained according to Example 3, are brought to reaction at 150°C with 13.35 g (50 mmols) of octadecylamine. A melt forms which is then stirred, yielding 39.7 g (97.4% of theory) of a light brown compound of the formula $$C_8F_{17}\text{—}CH_2\text{—}CH_2\text{—}SO_2\text{—}CH_2\text{—}CH_2\text{—}CO\text{—}NH(CH_2)_{17}CH_3 \quad (123)$$

which is soluble in hot benzene.

m.p.: 132° to 147°C.

calculated: C 44.55; H 5.55; N 1.68; S 3.84; F 38.64; found: C 44.69; H 5.53; N 1.77; S 3.84; F 37.4

APPLICATION EXAMPLES

Example 25

The compound of the formula (101) is sprayed in finely powdered form in an amount of 0.1% on a polyester/cotton fabric, or of 0.2% on a cotton fabric, of 0.05% on paper, and of 0.1% on dry leather, and subsequently heated for 30 seconds to 120°–125°C (5°–10°C above the melting point), so that a fine film is formed on the material. The materials finished in this way are oil and water-repellent. Similar results are attained also with the compounds according to Examples 2, 4 and 5.

Example 26

The compound of the formula (103) is dissolved in hexafluoroisopropanol. A cotton and wool/gabardine fabric is impregnated with a 2.5% solution in the immersion process and squeezed to a pick-up of 60 to 100%. The finished fabrics are oil repellent. The oil repellency values are about 100–110. With the same application, oil repellencies of 120–130 are attained with the compounds according to Examples 6, 7, and 11. Comparable results are also attained with the compounds according to Examples 12 to 24. (The oil repellency is tested according to the 3M Oil Repellency Test. The values in this test are between 0 and 150; this latter figure denotes the optimum oil repellency).

I claim:

1. A perfluoroalkyl compound of the formula $$R_f\text{—}CH_2CH_2\text{—}SO_x\text{—}C_mH_{2m}A$$

wherein $R_f$ is a perfluoroalkyl radical with 5 to 18 carbon atoms,

A is COOH, COOR,

R is alkyl with 1 to 20 carbon atoms, $x$ is 1 or 2 and $m$ is a whole number from 1 to 3, with the proviso that when A is carboxyl, then $m$ is only 1 if $x$ is 1.

2. A perfluoroalkyl compound according to claim 1, which correspond to the formula $$C_nF_{2n+1}CH_2CH_2\text{—}SO_x\text{—}C_mH_{2m}A_1$$

wherein $A_1$ is COOH, COOR, R is alkyl with 1 to 20 carbon atoms, $n$ is a whole number from 6 to 14, $x$ is 1 or 2 and $m$ is a whole number from 1 to 3, with the proviso that when $A_1$ is —COOH, then $m$ is only 1 if $x$ is 1.

3. A perfluoroalkyl compound according to claim 2, wherein R represents alkyl with 1 to 18 carbon atoms.

4. A perfluoroalkyl compound according to claim 2, which correspond to the formula $$C_nF_{2n+1}CH_2CH_2\text{—}SO_x(CH_2)_{m'}A_1$$

wherein $A_1$ is COOH, COOR, R represents alkyl with 1 to 20 carbon atoms, $n$ is a whole number from 6 to 14 and $m'$ and $x$ is each 1 or 2, with the proviso that when $A_1$ is —COOH, then $m'$ is only 1 if $x$ is 1.

5. A perfluoroalkyl compound according to claim 2, which correspond to the formula $$C_nF_{2n+1}CH_2CH_2\text{—}SO_x\text{—}C_mH_{2m}A_2$$

wherein $A_2$ is —COOH, $n$ is a whole number from 6 to 14, $x$ is 1 or 2 and $m$ is a whole number from 1 to 3, with the proviso that when $A_2$ is —COOH, then $m$ is only 1 if $x$ is 1.

6. A perfluoroalkyl compound according to claim 5, which correspond to the formula $$C_nF_{2n+1}CH_2CH_2\text{—}SO_x(CH_2)_{m'}A_2$$

wherein $A_2$ is —COOH, and $n$ is a whole number from 6 to 14 and $m'$ and $x$ is each 1 or 2, with the proviso that when $A_2$ is —COOH, then $m'$ is only 1 if $x$ is 1.

7. A perfluoroalkyl compound according to claim 2, which correspond to the formula $$C_nF_{2n+1}CH_2CH_2\text{—}SO_x\text{—}C_mH_{2m}COOR$$

wherein R represents alkyl with 1 to 20 carbon atoms, $n$ is a whole number from 6 to 14, $x$ is 1 or 2, and $m$ is a whole number from 1 to 3.

8. A perfluoroalkyl compound according to claim 7, which correspond to the formula $$C_nF_{2n+1}CH_2CH_2\text{—}SO_x(CH_2)_{m'}COOR$$

wherein R represents alkyl with 1 to 20 carbon atoms, $n$ is a whole number from 6 to 14, and $m'$ and $x$ is each 1 or 2.

9. A perfluoroalkyl compound according to claim 7, which is selected from the group consisting of the formulae $$C_nF_{2n+1}CH_2CH_2\text{—}SO\text{—}CH_2\text{—}\underset{\underset{CH_3}{|}}{CH}\text{—}COOR,$$

$$C_nF_{2n+1}CH_2CH_2\text{—}SO\text{—}\underset{\underset{CH_3}{|}}{CH}\text{—}CH_2\text{—}COOR,$$

$$C_nF_{2n+1}CH_2CH_2\text{—}SO_2\text{—}CH_2\underset{\underset{CH_3}{|}}{CH}\text{—}COOR \quad \text{and}$$

$$C_nF_{2n+1}CH_2CH_2\text{—}SO_2\text{—}\underset{\underset{CH_3}{|}}{CH}\text{—}CH_2\text{—}COOR$$

wherein

R is alkyl with 1 to 20 carbon atoms and $n$ is a whole number from 6 to 14.

10. A perfluoroalkyl compound according to claim 7, wherein R is alkyl with 1 to 18 carbon atoms.

11. A perfluoroalkyl compound according to claim 2, wherein $n$ is a whole number from 6 to 10.

* * * * *